(12) United States Patent
Zhang et al.

(10) Patent No.: US 10,589,104 B2
(45) Date of Patent: Mar. 17, 2020

(54) SYSTEMS AND METHODS FOR CREATING STIMULATION PROGRAMS BASED ON USER-DEFINED AREAS OR VOLUMES

(71) Applicant: Boston Scientific Neuromodulation Corporation, Valencia, CA (US)

(72) Inventors: Tianhe Zhang, Studio City, CA (US); G. Karl Steinke, Valencia, CA (US); Stephen Carcieri, Los Angeles, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 236 days.

(21) Appl. No.: 15/864,876

(22) Filed: Jan. 8, 2018

(65) Prior Publication Data

US 2018/0193655 A1 Jul. 12, 2018

Related U.S. Application Data

(60) Provisional application No. 62/444,724, filed on Jan. 10, 2017.

(51) Int. Cl.
*A61N 1/372* (2006.01)
*A61N 1/36* (2006.01)
*A61N 1/05* (2006.01)

(52) U.S. Cl.
CPC ....... *A61N 1/37247* (2013.01); *A61N 1/0534* (2013.01); *A61N 1/0551* (2013.01); *A61N 1/36062* (2017.08); *A61N 1/36185* (2013.01)

(58) Field of Classification Search
CPC ...... A61N 1/0534; A61N 1/0551; A61N 1/36; A61N 1/36062; A61N 1/36128;
(Continued)

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 1048320 11/2000
EP 1166819 1/2002
(Continued)

OTHER PUBLICATIONS

International Search Report and Written Opinion for PCT Application No. PCT/US2018/012807 dated Apr. 23, 2018.
(Continued)

*Primary Examiner* — Christopher A Flory
(74) *Attorney, Agent, or Firm* — Lowe Graham Jones PLLC; Bruce E. Black

(57) ABSTRACT

A method for generating a stimulation program for electrical stimulation of a patient includes providing, by a processor on a display, a first grid of first pixels and a representation of a portion of an electrical stimulation lead with electrodes; obtaining, by the processor, a user selection of a first set of the first pixels in the first grid for stimulation; generating, by the processor, a stimulation program based, at least in part, on the user-selected first set of first pixels for stimulation using at least one of the electrodes of the electrical stimulation lead; and initiating, by the processor, a signal that provides an implantable pulse generator with the stimulation program. In other methods, instead of a grid of pixels, user-selectable primitives or selectable-objects are used to determine a desired stimulation region and generate the stimulation program.

20 Claims, 9 Drawing Sheets

(58) Field of Classification Search
CPC ............ A61N 1/36132; A61N 1/36146; A61N 1/36185; A61N 1/37247; A61N 1/05; A61N 1/08; A61N 1/36125
USPC .................................................. 607/59, 72
See application file for complete search history.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,707,476 B1* | 3/2004 | Hochstedler ........ G06F 19/3418 715/789 |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |

(56) References Cited

U.S. PATENT DOCUMENTS

| | | |
|---|---|---|
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | DiLorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,450,997 B1 | 11/2008 | Pianca et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,664,849 B1 * | 2/2010 | Chandler ............ G06F 11/0727 709/224 |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,175,710 B2 | 5/2012 | Fie |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,429,174 B2 | 4/2013 | Ramani et al. |
| 8,452,415 B2 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,606,360 B2 | 12/2013 | Butson et al. |
| 8,620,452 B2 | 12/2013 | King et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Blum et al. |
| 9,248,272 B2 | 2/2016 | Romero |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezai |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155333 A1 * | 7/2006 | Goetz ................ A61N 1/36071 607/2 |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |

(56) References Cited

U.S. PATENT DOCUMENTS

| | | |
|---|---|---|
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1* | 8/2007 | Goetz .............. A61N 1/0529 607/59 |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1* | 8/2007 | Stone .............. A61N 1/0529 607/59 |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1* | 6/2008 | Goetz .............. A61N 1/36185 607/59 |
| 2008/0154341 A1 | 6/2008 | McIntyre et al. |
| 2008/0163097 A1* | 7/2008 | Goetz .............. A61N 1/36185 715/772 |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0043359 A1* | 2/2009 | Smoorenburg .... A61N 1/37247 607/57 |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1* | 11/2009 | Carlton .............. A61N 1/37247 607/45 |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1* | 1/2010 | Thacker .............. A61N 1/36071 607/46 |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1* | 2/2010 | Goetz ................ A61N 1/36071 607/59 |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1* | 5/2010 | Kothandaraman ......................... A61N 1/36185 607/46 |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0046697 A1* | 2/2011 | Gerber .................... A61N 1/08 607/59 |
| 2011/0066407 A1 | 3/2011 | Butson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0238129 A1 | 9/2011 | Moffitt |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |

(56) References Cited

U.S. PATENT DOCUMENTS

| | | |
|---|---|---|
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0296396 A1* | 11/2012 | Moffitt .............. G16H 40/63 607/59 |
| 2012/0302912 A1* | 11/2012 | Moffitt .............. A61N 1/36185 600/554 |
| 2012/0303087 A1* | 11/2012 | Moffitt .............. A61N 1/36185 607/45 |
| 2012/0314924 A1 | 12/2012 | Carlton et al. |
| 2012/0316615 A1 | 12/2012 | Digiore et al. |
| 2012/0316619 A1* | 12/2012 | Goetz ................ A61N 1/0534 607/59 |
| 2012/0330622 A1 | 12/2012 | Butson et al. |
| 2013/0039550 A1 | 2/2013 | Blum et al. |
| 2013/0041283 A1* | 2/2013 | Wichner .............. A61N 1/36 600/547 |
| 2013/0060304 A1* | 3/2013 | LaTendresse ...... A61N 1/36014 607/59 |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1* | 5/2013 | Carlton .............. A61N 1/37235 607/59 |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0226261 A1* | 8/2013 | Sparks ............... A61N 1/37247 607/45 |
| 2013/0261684 A1 | 10/2013 | Howard |
| 2013/0289380 A1 | 10/2013 | Molnar et al. |
| 2013/0304152 A1* | 11/2013 | Bradley ............. A61N 1/36071 607/46 |
| 2013/0317587 A1 | 11/2013 | Barker |
| 2013/0325091 A1 | 12/2013 | Pianca et al. |
| 2014/0005748 A1* | 1/2014 | Goetz ................ A61N 1/37247 607/59 |
| 2014/0039587 A1 | 2/2014 | Romero |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0081354 A1* | 3/2014 | Davis ................... A61N 1/372 607/59 |
| 2014/0122379 A1 | 5/2014 | Moffitt et al. |
| 2014/0276181 A1* | 9/2014 | Sun ..................... A61B 5/686 600/544 |
| 2014/0277284 A1 | 9/2014 | Chen et al. |
| 2014/0296953 A1 | 10/2014 | Pianca et al. |
| 2014/0324125 A1* | 10/2014 | Goetz .................... A61N 1/08 607/59 |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2014/0371819 A1* | 12/2014 | Goetz ................... A61N 1/0551 607/59 |
| 2015/0012057 A1* | 1/2015 | Carlson .............. A61N 1/37264 607/45 |
| 2015/0018915 A1 | 1/2015 | Leven |
| 2015/0021817 A1 | 1/2015 | Romero et al. |
| 2015/0022497 A1* | 1/2015 | Chang ................ G06F 3/0412 345/174 |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0134031 A1 | 5/2015 | Moffitt et al. |
| 2015/0151113 A1 | 6/2015 | Govea et al. |
| 2015/0238762 A1* | 8/2015 | Pal ....................... A61N 1/0476 607/45 |
| 2015/0297893 A1* | 10/2015 | Kokones ............ A61N 1/37247 607/45 |
| 2015/0328461 A1* | 11/2015 | Charlesworth .... A61N 1/36014 607/45 |
| 2015/0328467 A1* | 11/2015 | Demers .............. A61N 1/36014 607/45 |
| 2016/0022995 A1 | 1/2016 | Kothandaraman et al. |
| 2016/0023008 A1 | 1/2016 | Kothandaraman |
| 2016/0027293 A1* | 1/2016 | Esteller ................ A61B 5/686 340/517 |
| 2016/0030749 A1* | 2/2016 | Carcieri ............. A61N 1/36128 607/45 |
| 2016/0062499 A1* | 3/2016 | Pedder ................... G06F 3/041 345/174 |
| 2016/0074662 A1* | 3/2016 | Moffitt ............... A61N 1/36146 607/72 |
| 2016/0096025 A1 | 4/2016 | Moffitt et al. |
| 2016/0121126 A1* | 5/2016 | Marnfeldt .......... A61N 1/36167 607/59 |
| 2016/0136429 A1 | 5/2016 | Massoumi et al. |
| 2016/0136443 A1 | 5/2016 | Kothandaraman et al. |
| 2016/0199660 A1* | 7/2016 | Rao .................... A61N 1/37247 607/59 |
| 2016/0228692 A1 | 8/2016 | Steinke et al. |
| 2016/0256693 A1 | 9/2016 | Parramon |
| 2016/0375248 A1* | 12/2016 | Carcieri ............. A61N 1/36071 607/59 |
| 2016/0375258 A1 | 12/2016 | Steinke |
| 2017/0100593 A1 | 4/2017 | Zottola |
| 2017/0252570 A1 | 9/2017 | Serrano Carmona et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.

Obeso, J. A., et al., "Deep-brain stimulation of the subthalamic nucleus or the pars interna of the globus pallidus in Parkinson's disease.", N Engl J Med., 345{13l. The Deep-Brain Stimulation for Parkinson's Disease Study Group, (Sep. 27, 2001 ),956-63.

(56) References Cited

OTHER PUBLICATIONS

Butson et al., "Current Steering to control the volume of tissue activated during deep brain stimulation," vol. 1, No. 1, Dec. 3, 2007, pp. 7-15.
Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.
Phillips, M. D., et al., "Parkinson disease: pattern of functional MR imaging activation during deep brain stimulation of subthalamic nucleus—initial experience", Radiology 239(1). (Apr. 2008),209-16.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikal Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.
Olivier Commowick et al., "Using Frankenstein's Creature Paradigm to Build a Patient Specific Atlas," Sep. 20, 2009, Medical Image Computing and Computer-Assisted Intervention, pp. 993-1000.
Lotjonen J.M.P. et al., "Fast and robust multi-atlas segmentation of brain magnetic resonance images," NeuroImage, Academic Press, vol. 49, No. 3, Feb. 1, 2010, pp. 2352-2365.
McIntyre, C. C., et al., "How does deep brain stimulation work? Present understanding and future questions.", J Clin Neurophysiol. 21 (1 ). (Jan.-Feb. 2004 ),40-50.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986),974-977.
Rattay, F., "Analysis of the electrical excitation of CNS neurons", IEEE Transactions on Biomedical Engineering 45 (6). (Jun. 1998),766-772.
Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.
Rubinstein, J. T., et al., "Signal coding in cochlear implants: exploiting stochastic effects of electrical stimulation", Ann Otol Rhinol Laryngol Suppl., 191, (Sep. 2003), 14-9.
Schwan, H.P., et al., "The conductivity of living tissues.", Ann NY Acad Sci., 65(6). (AUQ., 1957),1007-13.
Taylor, R. S., et al., "Spinal cord stimulation for chronic back and leg pain and failed back surgery syndrome: a systematic review and analysis of prognostic factors", Spine 30(1 ). (Jan. 1, 2005), 152-60.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments—electrochemical considerations.", J Neurosci Methods, 142(2), (Mar. 30, 2005),251-65.
Vidailhet, M. , et al., "Bilateral deep-brain stimulation of the globus pallidus in primary generalized dystonia", N Engl J Med. 352(5) (Feb. 3, 2005),459-67.
Izad, Oliver, "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturalles (1901), 37:547-579.
Dice, Lee R., "Measures of the Amount of Ecologic Association Between Species," Ecology 26(3) (1945): 297-302. doi:10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/BF01908075.
Cover, T.M. et al., "Elements of information theory," (1991) John Wiley & Sons, New York. NY.
Meila, Marina, "Comparing Clusterings by the Variation of Information," Learning Theory and Kernel Machines (2003): 173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No. 1, pp. 1-8.
Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J. , et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004),719-28.
Wei, X. F., et al., "Current density distributions, field distributions and impedance analysis of segmented deep brain stimulation electrodes", J Neural Eng . . . 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004 ),2755-63.

(56) References Cited

OTHER PUBLICATIONS

Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12:// www.sci.utah.edu/cibc/software/index.html, MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.
Frankemolle, et al., "Reversing cognitive-motor impairments in Parkinson's disease patients using a computational modelling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006), 132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).

Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102(5) pp. 363-367 May 1993.
Bedard, C. , et al., "Modeling extracellular field potentials and the frequency-filtering properties of extracellular space", Biophys J .. 86(3). (Mar. 2004), 1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS'06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention—Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging." Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the

(56) References Cited

OTHER PUBLICATIONS

Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of afterpotentials on the recovery cycle," J Neurophysiol, 87(2) (Feb. 2002), pp. 995-1006.
Mcintyre, Cameron C., et al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern., 79(1) (Jul. 1998), pp. 29-37.
Mcintyre, Cameron C., et al., "Uncovering the mechanism(s) of action of deep brain stimulation: activation, inhibition, or both," Clin Neurophysiol, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59 (5) (Sep. 10, 2002), pp. 706-713.
Nowak. LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg, Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
Sl. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.
Testerman, Roy L., "Coritical response to callosal stimulation: A model for determining safe and efficient stimulus parameters," Annals of Biomedical Engineering, 6(4) (1978), pp. 438-452.

(56) References Cited

OTHER PUBLICATIONS

Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 96(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilater high-frequency stimulation in the subthalamic nucleus for the treatment of Parkinson disease: correlation of therapeutic efftect with anatomical electrode position," J. Neurosurg., 96(2) (Feb. 2002), pp. 269-279.
Wakana, S., et al., "Fiber tract-based atlas of human white matter anatomy," Radioloy, 230(1) (Jan. 2004) pp. 77-87.
Alexander, DC., et al., "Spatial transformations of diffusion tensor magnetic resonance images," IEEE Transactions on Medical Imaging, 20 (11), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al. "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R, et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (lhalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16(6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul. 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atlas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K.W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes In Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

(56) References Cited

OTHER PUBLICATIONS

Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anaheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I, Atlas Construction Based on Immunohistochemical and MRI Data", NeuroImage, 34:618-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.

(56) References Cited

OTHER PUBLICATIONS

An, et al., "Prefronlal cortical projections to longitudinal columns in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T., et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The NEURON simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Funel. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
McIntyre, Cameron, et al., "Finite element analysis of the current-density and electric field generated by metal microelectrodes", Ann Biomed Eng . 29(3), (2001 ),227-235.
Foster, K. R., et al., "Dielectric properties of tissues and biologicai materials: a critical review.", Grit Rev Biomed Ena. 17(1 ). {1989),25-104.
Limousin, P., et al., "Electrical stimulation of the subthalamic nucleus in advanced Parkinson's disease", N Engl J Med .. 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1), (Apr. 1, 2000),45-50.
Hines, M. L., et al., "The NEURON simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S. , et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T. , et al., "Stimulation of the subthalamic nucleus changes the firing pattern of pallidal neurons", J Neurosci. 23(5). (Mar. 1, 2003),1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
McNaughtan et al., "Electrochemical Issues in Impedance Tomography", 1st World Congress on Industrial Process Tomography, Buxton, Greater Manchester, Apr. 14-17, 1999.
Grill, WM., et al., "Electrical properties of implant encapsulation tissue", Ann Biomed Eng. vol. 22. (1994),23-33.

(56) References Cited

OTHER PUBLICATIONS

Grill, W. M., et al., "Deep brain stimulation creates an informational lesion of the stimulated nucleus", Neuroreport. 15l7t (May 19, 2004), 1137-40.

Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.

* cited by examiner

SYSTEMS AND METHODS FOR CREATING STIMULATION PROGRAMS BASED ON USER-DEFINED AREAS OR VOLUMES

CROSS-REFERENCE TO RELATED APPLICATIONS

This application claims the benefit under 35 U.S.C. § 119(e) of U.S. Provisional Patent Application Ser. No. 62/444,724, filed Jan. 10, 2017, which is incorporated herein by reference.

FIELD

The present invention is directed to the area of implantable electrical stimulation systems and methods of making and using the systems. The present invention is also directed to systems and methods for generating a stimulation program for electrical stimulation of a patient.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), at least one lead, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a method for generating a stimulation program for electrical stimulation of a patient. The method includes providing, by a processor on a display communicatively coupled to the processor, a first grid demarcating a plurality of selectable first pixels and a representation of a portion of an electrical stimulation lead with a plurality of electrodes; obtaining, by the processor, a user selection of a first plurality of the first pixels in the first grid of first pixels for stimulation; generating, by the processor, a stimulation program based, at least in part, on the user-selected first plurality of the first pixels for stimulation using at least one of the electrodes of the electrical stimulation lead; and initiating, by the processor, a signal that provides an implantable pulse generator with the stimulation program for producing electrical stimulation using an electrical stimulation lead coupled to the implantable pulse generator in accordance with the stimulation program.

In at least some embodiments, generating the stimulation program includes: determining, by the processor, a target volume based, at least in part, on the user-selected first plurality of the first pixels for stimulation; determining, by the processor, a stimulation field model (SFM) based, at least in part, on the determined target volume; and generating, by the processor, the stimulation program based, at least in part, on the SFM.

In at least some embodiments, the method further includes: providing, by the processor on the display, a second grid demarcating a plurality of selectable second pixels, the second grid of second pixels residing on a different plane than a plane on which the first grid of first pixels resides; and obtaining, by the processor, a user selection of a plurality of the second pixels in the second grid of second pixels for stimulation, wherein determining the target volume includes determining, by the processor, the target volume based, at least in part, on both the user-selected first plurality of the first pixels for stimulation and the user-selected plurality of the second pixels for stimulation.

In at least some embodiments, providing the first grid of first pixels includes providing, by the processor on the display, a view of the first grid of first pixels, wherein the view shows the first grid of first pixels in relation to a representation of at least one anatomical or physiological feature.

In at least some embodiments, the method further includes obtaining, by the processor, a user selection of a second plurality of the first pixels in the first grid of first pixels to avoid stimulation, wherein generating the stimulation program includes: determining, by the processor, a first volume based, at least in part, on the user-selected first plurality of the first pixels for stimulation; determining, by the processor, a second volume based, at least in part, on the user-selected second plurality of the first pixels to avoid stimulation; determining, by the processor, a stimulation field model (SFM) based, at least in part, on the first and second determined volumes; and generating, by the processor, the stimulation program based, at least in part, on the SFM.

In at least some embodiments, generating the stimulation program includes: matching, by the processor, the user-selected first plurality of the first pixels for stimulation to a stimulation field model (SFM) stored in a memory communicatively coupled to the processor; selecting, by the processor, at least one of the electrodes of the electrical stimulation lead based, at least in part, on the SFM; selecting, by the processor, a set of stimulation parameters based, at least in part, on the SFM; and generating, by the processor, the stimulation program.

In at least some embodiments, the method further includes obtaining, by the processor, a user input representing a stimulation level for each one of the user-selected first plurality of the first pixels for stimulation, wherein generating the stimulation program includes generating, by the processor, the stimulation program based, at least in part, on the user-selected first plurality of the first pixels for stimulation and on the user-input stimulation level for each one of the user-selected first plurality of the first pixels for stimulation.

In at least some embodiments, the method further includes superimposing the first grid of first pixels on a representation of at least one anatomical or physiological feature.

Another embodiment is a method for generating a stimulation program for electrical stimulation of a patient. The method includes providing, by processor on a display communicatively coupled to the processor, a portion of a first plane; obtaining, by the processor, a user placement of a first primitive onto the first plane for stimulation; obtaining, by the processor, a user input of a command to modify at least one feature of the user-placed first primitive for stimulation; generating, by the processor, a stimulation program based, at least in part, on the modified user-placed first primitive for stimulation; and initiating, by the processor, a signal that provides an implantable pulse generator with the stimulation program for producing electrical stimulation using an electrical stimulation lead coupled to the implantable pulse generator in accordance with the stimulation program.

In at least some embodiments, generating the stimulation program includes: determining, by the processor, a target volume based, at least in part, on the modified user-placed first primitive for stimulation; determining, by the processor, a stimulation field model (SFM) based, at least in part, on the determined target volume; and generating, by the processor, the stimulation program based, at least in part, on the SFM.

In at least some embodiments, the method further includes providing, by the processor on the display, a portion of a second plane different from the first plane; obtaining, by the processor, a user placement of a second primitive onto the second plane; and obtaining, by the processor, a user input of a command to modify at least one feature of the user-placed second primitive for stimulation, wherein determining the target volume includes determining, by the processor, the target volume based, at least in part, on both the modified user-placed first primitive for stimulation and the modified user-placed second primitive for stimulation.

In at least some embodiments, obtaining the user input of the command to modify the at least one feature of the user-placed first primitive for stimulation includes obtaining, by the processor, a user input of a command to alter a shape of the user-placed first primitive for stimulation along at least one dimension of the user-placed first primitive for stimulation.

In at least some embodiments, the method further includes obtaining, by the processor, a user placement of a second primitive onto the first plane to avoid stimulation, wherein generating the stimulation program includes: determining, by the processor, a first volume based, at least in part, on the modified user-placed first primitive for stimulation; determining, by the processor, a second volume based, at least in part, on the user-placed second primitive to avoid stimulation; determining, by the processor, a stimulation field model (SFM) based, at least in part, on the first and second determined volumes; and generating, by the processor, the stimulation program based, at least in part, on the SFM, wherein the stimulation program, when implemented by the implantable pulse generator, causes the implantable pulse generator to stimulate the first determined volume and to avoid stimulation of the second determined volume.

In at least some embodiments, determining the SFM includes determining when the second determined volume overlaps at least one portion of first determined volume; and generating the stimulation program based, at least in part, on the SFM includes, responsive to the second determined volume overlapping the at least one portion of the first determined volume, generating, by the processor, the stimulation program based, at least in part, on the SFM, wherein the stimulation program, when implemented by the implantable pulse generator, causes the implantable pulse generator to stimulate at least one portion of the first determined volume that the second determined volume fails to overlap and to avoid stimulation of at least one portion of the second determined volume.

In at least some embodiments, the method further includes obtaining, by the processor, a user input of a command to modify at least one feature of the user-placed second primitive to avoid stimulation, wherein determining the second volume includes determining, by the processor, the second volume based, at least in part, on the modified user-placed second primitive to avoid stimulation.

In at least some embodiments, generating the stimulation program includes: matching, by the processor, the modified user-placed first primitive to a stimulation field model (SFM) stored in a memory communicatively coupled to the processor; selecting, by the processor, a set of stimulation electrodes from the electrodes of the electrical stimulation lead based, at least in part, on the SFM; selecting, by the processor, a set of stimulation parameters based, at least in part, on the SFM; and generating, by the processor, the stimulation program, wherein the stimulation program, when implemented by the implantable pulse generator, causes the implantable pulse generator to stimulate the patient via the set of stimulation electrodes according to the set of stimulation parameters.

Yet another embodiment is a non-transitory computer-readable medium having computer executable instructions stored thereon that, when executed by at least one processor, cause the at least one processor to perform any of the methods described above.

A further embodiment is a system for generating a stimulation program for electrical stimulation of a patient, the system including processor configured and arranged to perform any of the methods described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
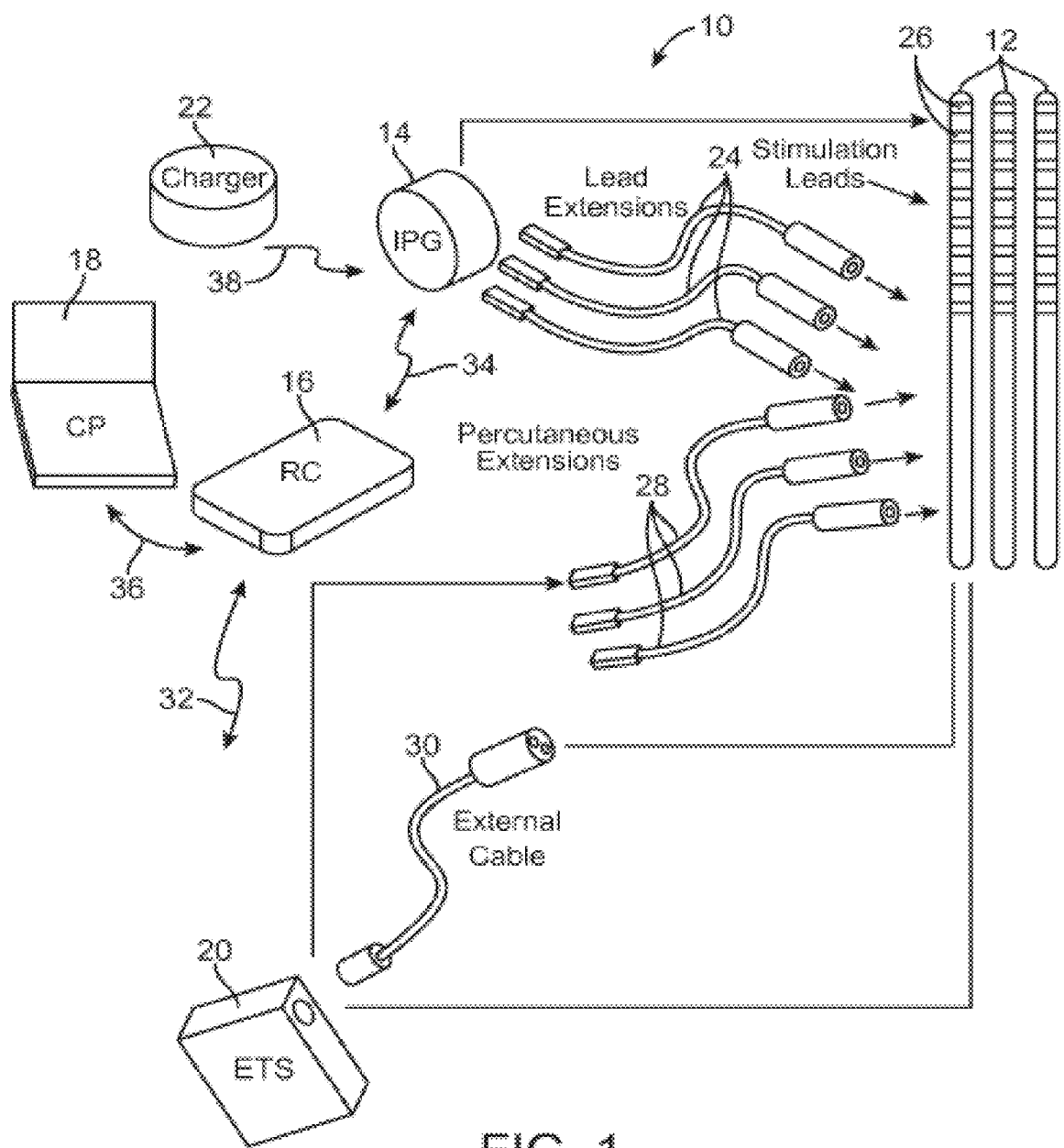
FIG. 1 is a schematic view of one embodiment of an electrical stimulation system, according to the invention.

The present invention is directed to the area of implantable electrical stimulation systems and methods of making and using the systems. The present invention is also directed to systems and methods for selecting stimulation parameters.

Suitable implantable electrical stimulation systems include, but are not limited to, a least one lead with at least one electrode disposed on a distal end portion of the lead and at least one terminal disposed on at least one proximal end portion of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position or across a particular longitudinal region. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves, muscles, and tissues. In particular, stimulation may stimulate specific targets. Examples of such targets include, but are not limited to, the subthalamic nucleus (STN), internal segment of the globus pallidus (GPi), external segment of the globus pallidus (GPe), and the like. In at least some embodiments, an anatomical structure is defined by its physical structure and a physiological target is defined by its functional attributes. In at least some embodiments, the lead may be positioned at least partially within the target, but in other embodiments, the lead may be near, but not inside, the target. The stimulation of tissue can include, but is not limited to, one or more of activation, inhibition, depression, or other modulation of the stimulated tissue.

Turning to FIG. 1, one embodiment of an electrical stimulation system 10 includes at least one stimulation lead 12 and an implantable pulse generator (IPG) 14. The system 10 can also include at least one of an external remote control (RC) 16, a clinician's programmer (CP) 18, an external trial stimulator (ETS) 20, or an external charger 22.

The IPG 14 is physically connected, optionally via at least one lead extension 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The IPG 14 can be implanted into a patient's body, for example, below the patient's clavicle area or within the patient's buttocks or abdominal cavity. The IPG 14 can have eight stimulation channels which may be independently programmable to control the magnitude of the current stimulus from each channel. In at least some embodiments, the IPG 14 can have more or fewer than eight stimulation channels (for example, 4-, 6-, 16-, 32-, or more stimulation channels). The IPG 14 can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test functioning of the system or the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706;

8,175,710; 8,224,450; and 8,364,278; and U.S. Patent Application Publication No. 2007/0150036, as well as the other references cited above, all of which are incorporated by reference.

Figure 2:
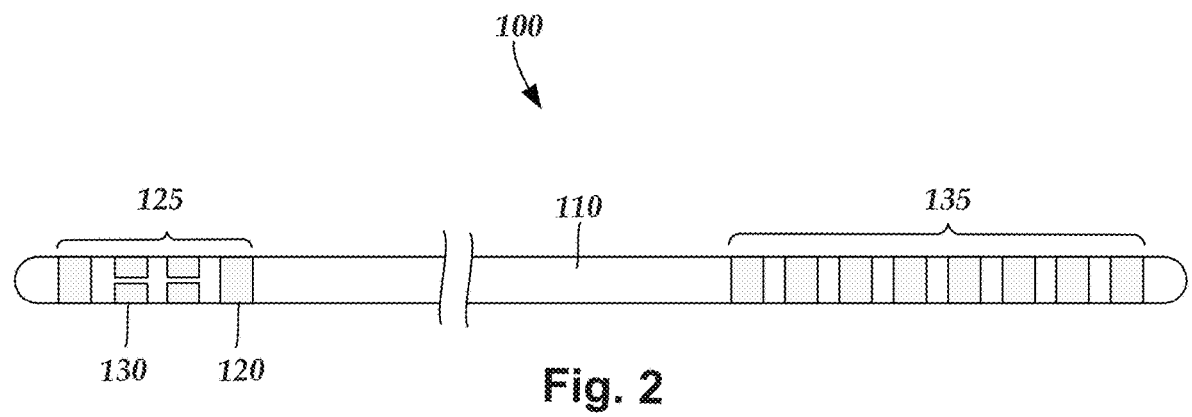
FIG. 2 is a schematic side view of one embodiment of an electrical stimulation lead, according to the invention.

FIG. 2 illustrates one embodiment of a lead 100 with electrodes 125 disposed at least partially about a circumference of the lead 100 along a distal end portion of the lead 100 and terminals 135 disposed along a proximal end portion of the lead 100. The lead 100 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of a stylet (not shown). The lead 100 can be guided to the target location within the brain using, for example, a stereotactic frame and a microdrive motor system. In at least some embodiments, the microdrive motor system can be fully or partially automatic. The microdrive motor system may be configured to perform at least one of the following actions (alone or in combination): insert the lead 100, advance the lead 100, retract the lead 100, or rotate the lead 100.

In at least some embodiments, measurement devices coupled to the muscles or other tissues affected by the target neurons or neural structures, or a unit responsive to the patient or clinician, can be coupled to the IPG 14 or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 100 for deep brain stimulation can include stimulation electrodes, recording electrodes, or both. In at least some embodiments, the lead 100 is rotatable so that the stimulation electrodes can be aligned with the target neurons after the neurons have been located using the recording electrodes.

Stimulation electrodes may be disposed on the circumference of the lead 100 to stimulate the target neurons. Stimulation electrodes may be ring shaped so that current projects from each electrode equally in every direction from the position of the electrode along a length of the lead 100. In the embodiment of FIG. 2, two of the electrodes 125 are ring electrodes 120. Ring electrodes typically do not enable stimulus current to be directed from only a limited angular range around a lead. Segmented electrodes 130, however, can be used to direct stimulus current to a selected angular range around a lead. When segmented electrodes are used in conjunction with an implantable pulse generator that delivers constant current stimulus, current steering can be achieved to more precisely deliver the stimulus to a position around an axis of a lead (i.e., radial positioning around the axis of a lead). To achieve current steering, segmented electrodes can be utilized in addition to, or as an alternative to, ring electrodes.

The lead 100 includes a lead body 110, terminals 135, at least one ring electrode 120, and at least one set of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes 125 are made of a material that is biocompatible and does not substantially corrode under expected operating conditions in the operating environment for the expected duration of use.

Each of the electrodes 125 can either be used or unused (OFF). When an electrode is used, the electrode can be used as an anode or cathode and carry anodic or cathodic current. In some instances, an electrode might be an anode for a period of time and a cathode for a period of time.

Deep brain stimulation leads may include at least one set of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference.

Figure 3:
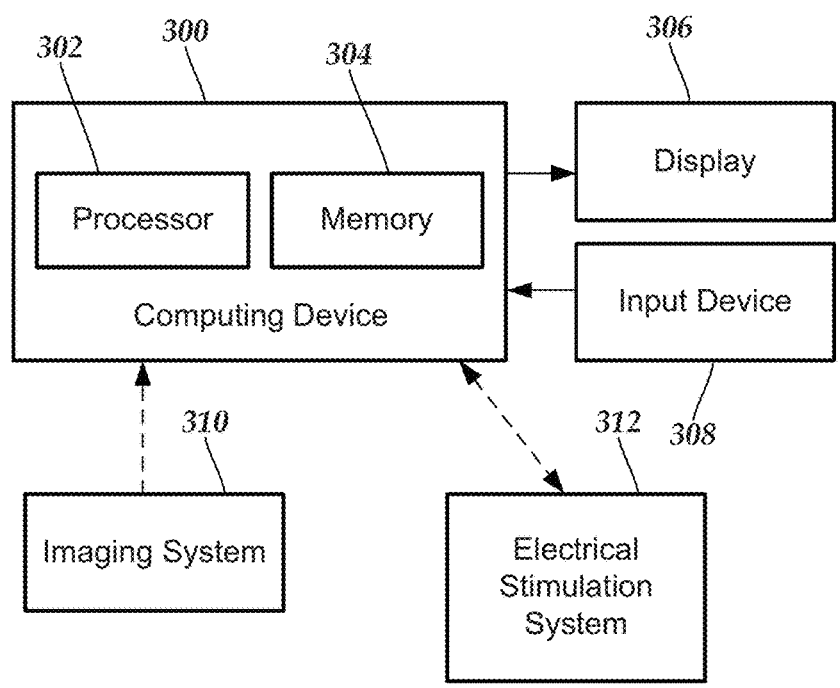
FIG. 3 is a schematic block diagram of one embodiment of a system for determining stimulation parameters, according to the invention.

FIG. 3 illustrates one embodiment of a system for practicing the invention. The system can include a computing device 300 or any other similar device that includes a processor 302 and a memory 304, a display 306, an input device 308, and, optionally, an electrical stimulation system 312. The system 300 may also optionally include at least one imaging system 310.

The computing device 300 can be a computer, tablet, mobile device, or any other suitable device for processing information. The computing device 300 can be local to the user or can include components that are non-local to the computer including one or both of the processor 302 or memory 304 (or portions thereof). For example, in at least some embodiments, the user may operate a terminal that is connected to a non-local computing device. In other embodiments, the memory can be non-local to the user.

The computing device 300 can utilize any suitable processor 302 including at least one hardware processors that may be local to the user or non-local to the user or other components of the computing device. The processor 302 is configured to execute instructions provided to the processor 302, as described below.

Any suitable memory 304 can be used for the computing device 302. The memory 304 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has at least one of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 306 can be any suitable display device, such as a monitor, screen, display, or the like, and can include a printer. The input device 308 can be, for example, a keyboard, mouse, touch screen, track ball, joystick, voice recognition system, or any combination thereof, or the like.

At least one imaging system 310 can be used including, but not limited to, MRI, computed tomography (CT), ultrasound, or other imaging systems. The imaging system 310 may communicate through a wired or wireless connection with the computing device 300 or, alternatively or additionally, a user can provide images from the imaging system 310 using a computer-readable medium or by some other mechanism.

The electrical stimulation system 312 can include, for example, any of the components illustrated in FIG. 1. The electrical stimulation system 312 may communicate with the computing device 300 through a wired or wireless connection or, alternatively or additionally, a user can provide information between the electrical stimulation system 312 and the computing device 300 using a computer-readable medium or by some other mechanism. In at least some embodiments, the computing device 300 may include part of the electrical stimulation system, such as, for example, the IPG 14, CP 18, RC 16, ETS 20, or any combination thereof.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (for example, RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It has been found that users may fail to understand or accurately predict effects of particular stimulation parameters on a desired portion of patient tissue when programming stimulation parameters for the IPG 14 and ETS 20 (for example, in the operating room or in follow-up sessions). Accordingly, the stimulation system may fail to sufficiently stimulate, may completely fail to stimulate, or may adversely stimulate the patient tissue.

Figure 4:
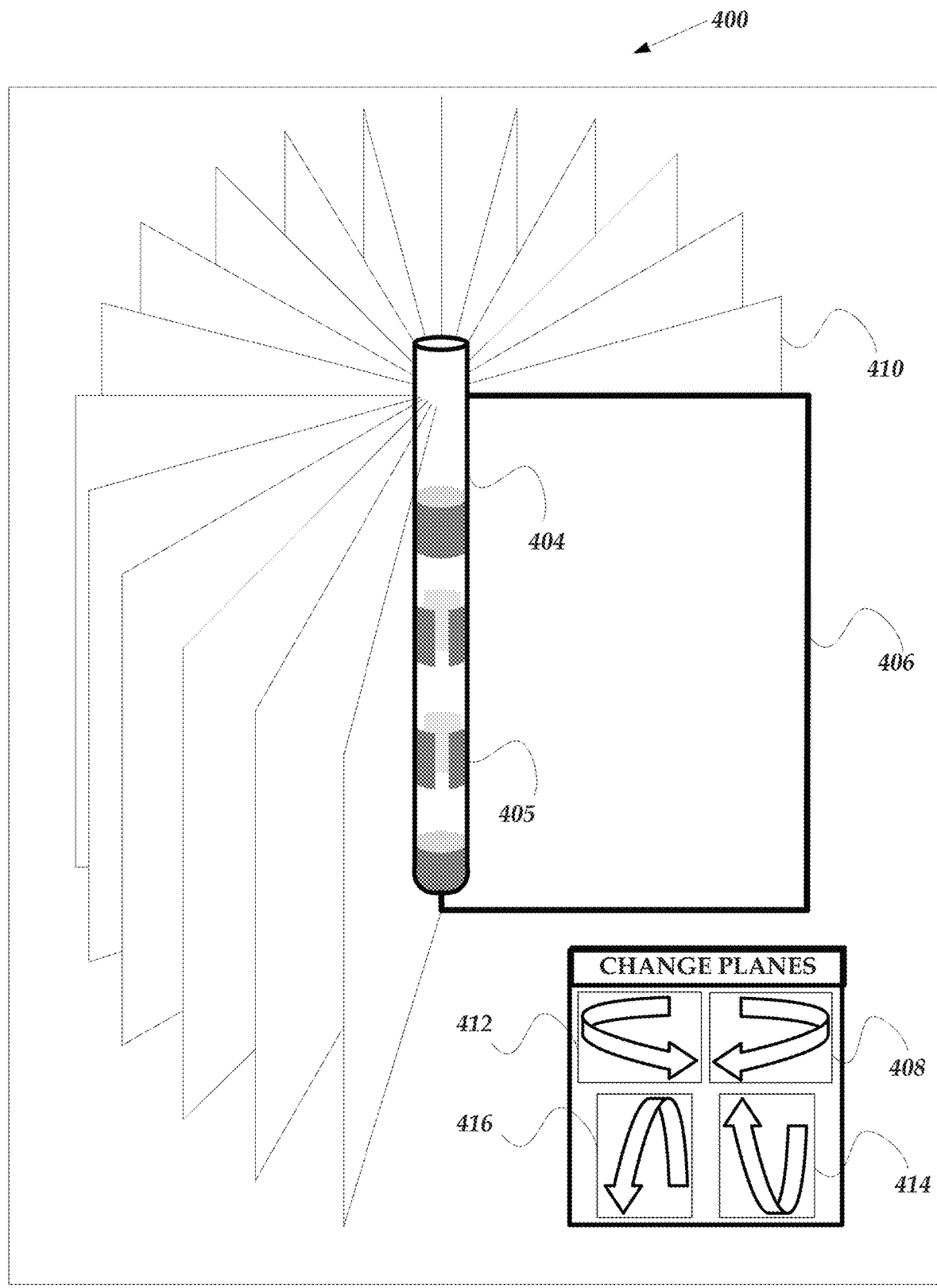
FIG. 4 is a graphical illustration of one embodiment of a user interface for selecting a plane to employ in at least one method for generating a stimulation program, according to the invention.

The present systems or methods facilitate the development of stimulation programs and the selection of stimulation parameters. FIG. 4 illustrates one embodiment of a user interface 400 for generating a stimulation program. In this particular user interface 400, the user can select a plane 406 in which to produce a stimulation area around a representation 404 of a distal portion (or any other suitable portion) of a lead. The representation 404 of the lead may include a captured image or a simulated image or model of the lead. In the illustrated embodiment, the planes 406 are parallel to the longitudinal axis of the lead. It will be understood, however, that planes of other orientation can be used including, but not limited to, planes perpendicular to the longitudinal axis of the lead.

The user interface 400 also includes multiple selectable planes 406, 410. In at least some embodiments, the planes 406, 410 are each a bounded two-dimensional region which corresponds to a two-dimensional region in three-dimensional space around a lead in a patient (or a future position of a lead to be implanted in the patient). In at least some embodiments, the planes each intersect, border or are near or adjacent the lead representation 404. In at least some embodiments, the planes intersect a longitudinal axis or a surface of the lead representation 404.

In at least some embodiments, the user interface 400 also includes representations (not shown) of at least one anatomical or physiological feature. In at least some embodiments, these representations may be captured images or simulated images or models of the anatomical or physiological features.

The user interface 400 can permit a user to select any of the selectable planes 406, 410. In at least some embodiments, the user interface 400 may emphasize the selected plane 406. In at least some embodiments, the user interface 400 may simultaneously display at least one other plane 410 for potential selection by the user. In some embodiments, actions or selections taken with respect to one plane may limit or restrict actions that can be taken in another plane or may increase or provide additional actions that can be taken in the other plane. This other plane or planes may be planes that having the same orientation or a different (for example, perpendicular) orientation to the first plane. In some embodiments, selections or other actions taken in a plane other than the currently selected plane may be displayed in the corresponding plane.

In at least some embodiments, the user interface 400 also includes one or more controls for selection by the user. The controls permit the user to change between different planes 406, 410. As an example, in the illustrated embodiment, selection of the first user control 408 causes the user interface to display and, optionally, highlight a subsequent plane 410 in the set of planes. In at least some embodiments, selection by the user of the first user control 408 may cause the user interface 400 to remove the initial plane 406 from view and display the subsequent plane 410.

Selection by the user of a second user control 412 causes the user interface to display and, optionally, highlight a prior plane (not shown) in the set of planes. The selection by the user of the second user control 412, when following the selection of the first user control 408 by the user, may cause the user interface 400 to return to the plane 406.

In at least some embodiments, the interface 400 can include one or more controls for viewing a second, distinct set of planes. In at least some embodiments, each plane in the second set of planes may be orthogonal to each plane in the first set of planes. As an example, selection by the user of a third user control 414 may cause the user interface 400 to display at least one plane in a second set of planes as seen from a distal tip of the lead 404 (for example, the rounded tip of the lead representation 404 shown by FIG. 4). As another example, selection by the user of a fourth user control 416 may cause the user interface 400 to provide at least one view of the second set of planes as seen from a proximal perspective relative to of the lead 404 (for example, the top of the lead representation 404 shown by FIG. 4).

In at least some embodiments, the user interface 400 may, responsive to displaying the second set of planes, replace the user controls 408 and 412 with user controls to scroll through the second set of planes. In at least some embodiments, the user interface 400 may, responsive to a selection of either of the user controls 414 or 416 while the user interface 400 displays the second set of planes, return to displaying the first set of planes. It will be understood that instead of controls provided on the user interface 400, in at least some embodiments, such controls may be operated in response to hand gestures.

Figure 5:
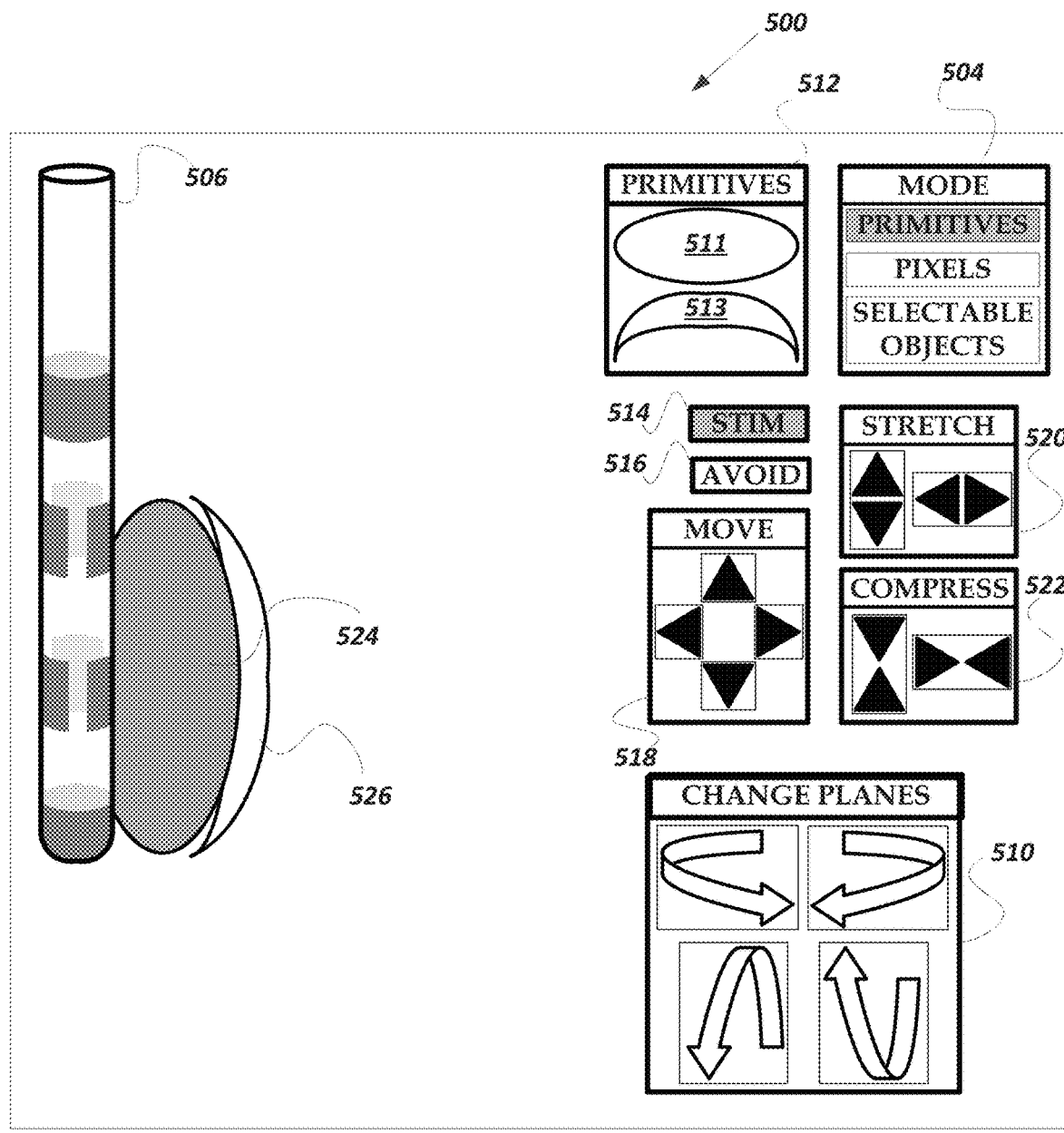
FIG. 5 is a graphical illustration of one embodiment of a user interface for user placement and user modification of at least one primitive on a plane for stimulation, according to the invention.

FIG. 5 illustrates one embodiment of a user interface 500 for generating a stimulation program. In this particular user interface 500, the user can place at least one primitive within the interface for stimulation. The lead representation 506 may be the same as or similar to the lead representation 404 of FIG. 4. The controls in box 510 may be the same as or similar to the controls 408, 412, 414, and 416 of FIG. 4. The user interface 500 may include a mode control 504 for moving between different modes for forming a stimulation region. In FIG. 5, the "primitives" mode is selected.

In at least some embodiments, the interface 500 may also define planes analogous to the plane 406 illustrated in FIG. 4, and the interface may permit the user to move through a set of planes similar to moving through the set of planes described above with respect to the interface 400.

In at least some embodiments, the user interface 500 may include one or more potential-primitive controls 512. In at least some embodiments, the potential-primitive controls 512 may include at least one potential primitive 511, 513 for the user to place onto the interface. In the illustrated embodiment of FIG. 5, the potential-primitive control 512 include an oval primitive 511 and a crescent primitive 513. Additional or alternative potential primitives may include, for example, circular, rectangular, square, trapezoidal, triangular, hexagonal, or octagonal primitives, any other suitable regular or irregular shape, or the like. Responsive to a user placement (for example, via drag-and-drop, click, or the like) of a primitive from the potential-primitive control 512 onto the interface, the user interface 500 shows the user-placed primitive (for example, at a position and with an orientation specified by the user placement).

In at least some embodiments, the user interface 500 may include one or more primitive-designation controls. In the illustrated embodiment of FIG. 5, the primitive-designation controls include a stimulation-designation control 514 and an avoid-designation control 516. Operation of stimulation-designation control 514 identifies a selected primitive 524 as a region to be stimulated. Operation of avoid-designation control 516 identifies a selected primitive 526 as a region where stimulation is to be avoided. In the interface 500, these two different statuses of the primitives can be distinguished via, for example, differences in coloring, shading, patterns, or other graphical indicia or any combination thereof. In at least some embodiments, the user may select at least one primitive (for example, via tapping, dragging a finger or cursor over, or circling at least one primitive in the interface 500) and then select either the stimulation-designation control 514 or the avoid-designation control 516. In at least some embodiments, the user may operate the primitive-designation controls prior to or subsequent to user placement of a primitive onto the interface 500.

In at least some embodiments, the user interface 500 may include at least one primitive-movement control 518 to move a user-placed primitive within the interface in a direction or manner that corresponds to the user-operated primitive-movement control. User operation of these and other controls may be one or more of tap or click a control, press-and-hold or click-and-hold a control, or a hand gesture (for example, such as finger-drag in a predefined direction along at least one of a user-placed primitive or plane in the interface 500). Other controls, not shown, may pivot or rotate a user-placed primitive about at least one point (for example, a center of gravity of the primitive or a user-selected point). In some embodiments, controls may be used to change a primitive from one type (for example, a circle) to another type (for example, a hexagon or square).

In the illustrated embodiment of FIG. 5, the user interface 500 includes primitive-stretch controls 520 and primitive-compress controls 522. These controls can be used to stretch or compress a user-placed primitive along at least one dimension (for example, a dimension specified by at least one of the user operation or the user-operated primitive-stretch controls 520 or primitive-compress controls 522). In at least some embodiments, these controls may also be employed via at least one sizing handle (not shown) that appears on or around a selected user-placed primitive.

In the illustrated embodiment of FIG. 5, the user interface 500 may, responsive to determining that the user-placed first primitive 524 and the user-placed second primitive 526 overlap each other and that the user-placed first and second primitives 524 and 526 have different designations (for example, stimulate and avoid), show the user-placed first primitive 524 as being behind the user-placed second primitive 526. For example, the user-placed second primitive 526 that has been designated to avoid stimulation may block the user's view of an overlapped portion of the user-placed first primitive 524 that has been designated for stimulation.

Figure 6:
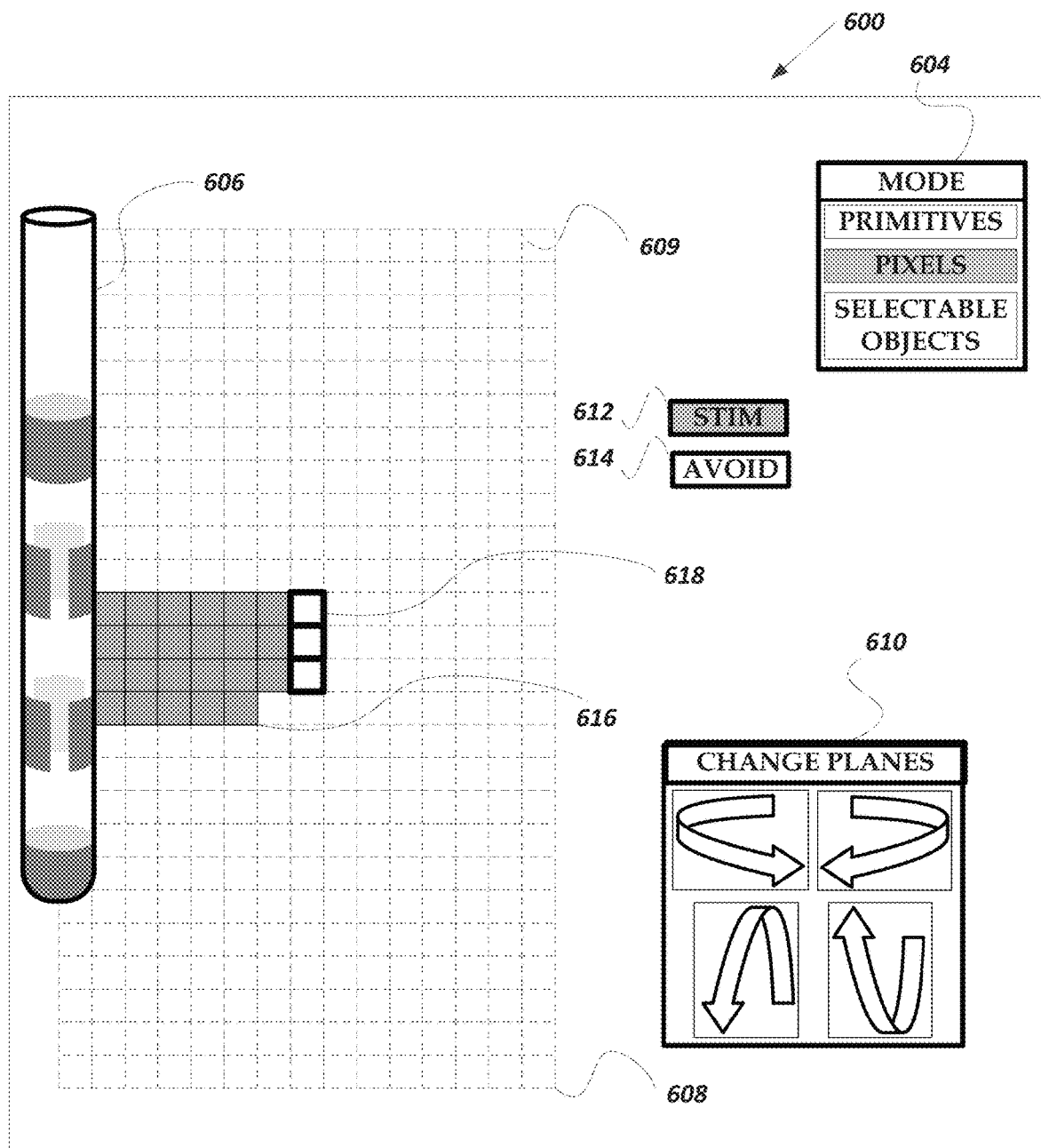
FIG. 6 is a graphical illustration of one embodiment of a user interface for user selection of a first plurality of pixels for stimulation, according to the invention.

FIG. 6 illustrates another embodiment of a user interface 600 for generating a stimulation program that allows the user to select one or more pixels 609, demarcated by a grid 608, for stimulation. The lead representation 606 may be the same as or similar to the lead representation 404 of FIG. 4.

The controls 604, 610, 612, 614 may be the same as or similar to controls of the user interfaces 400 or 500, as described above. In this embodiment, the mode in mode control 604 is set to "pixels". It will be understood that the pixels 609 are not pixels of a display on which the user interface 600 is displayed, but rather are regions demarcated by the grid 608 on the user interface. The pixels 609 may be rectangular, square, or any other suitable shape and may represent a two-dimensional or three-dimensional region of space around the lead.

In at least some embodiments, this grid 608 is analogous to the plane 406 illustrated in FIG. 4, and the interface 600 may permit the user to move through a set of grids similar to moving through the set of planes described above with respect to the interface 400. The planar controls 610 can be used to move among grids similar to the manner in which the planar controls 408, 412, 414, 416 are used to move through planes in interface 400.

In at least some embodiments, the user interface 600 may include at least one pixel-designation control such as a stimulation-designation control 612 and an avoid-designation control 614 that, when operated, cause a user-selected pixel to be designated for stimulation (for example, user-selected pixels 616) or designated to avoid stimulation (for example, user-selected pixels 618), respectively. These two different types of pixels can be distinguished visually or graphically using coloring, shading, patterns, or other graphical indicia or any combination thereof. In at least some embodiments, the user may select at least one pixel at a time (for example, via tapping, dragging a finger or cursor over, or circling at least one pixel in the grid of pixels 608). In at least some embodiments, the user may control a status of a user-selected pixel by operating at least one of the pixel-designation controls 612, 614 prior to or subsequent to user selection of the user-selected pixel.

Figure 7:
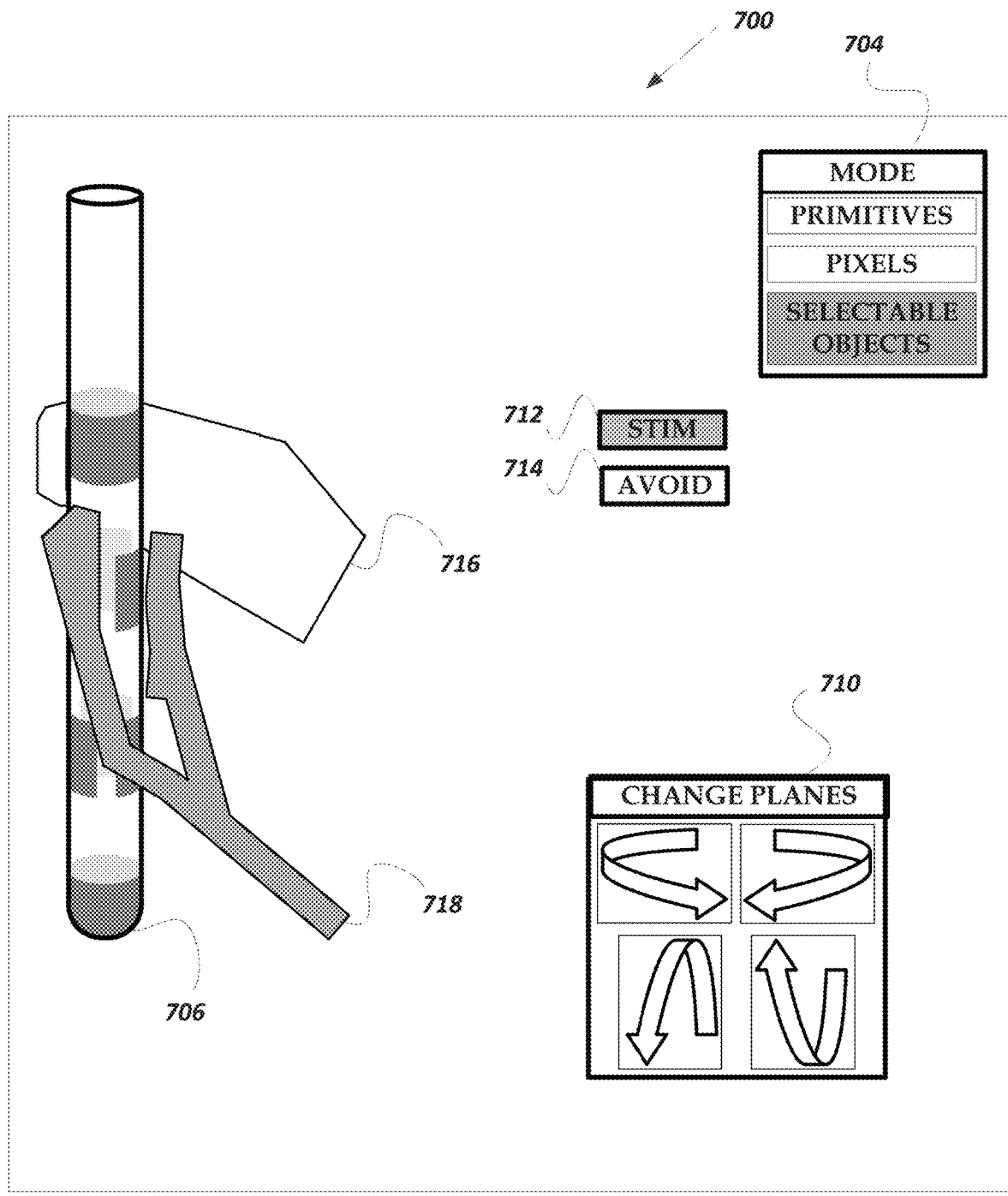
FIG. 7 is a graphical illustration of one embodiment of a user interface for user election of at least one selectable object for stimulation, according to the invention.

FIG. 7 illustrates yet another embodiment of a user interface 700 for generating a stimulation program one or more selectable (for example, clickable) objects 716, 718 for stimulation. The lead representation 706 may be the same as or similar to the lead representation 404 of FIG. 4. The controls 704, 710, 712, 714 may be the same as or similar to controls of the user interfaces 400, 500, or 600, as described above. In this embodiment, the mode in mode control 704 is set to "selectable objects".

In at least some embodiments, the interface 700 may also define planes analogous to the plane 406 illustrated in FIG. 4, and the interface may permit the user to move through a set of planes similar to moving through the set of planes described above with respect to the interface 400.

In at least some embodiments, the user interface 700 may include at least one selectable object 716, 718 in the interface. In at least some embodiments, a selectable object may graphically represent at least one anatomical or physiological feature or some other region, area, or volume that is previously or contemporaneously defined. In at least some embodiments, a selectable object may include a captured image or a simulated image or a model of an anatomical or physiological feature (an entirety or a portion of the anatomical or physiological feature).

In at least some embodiments, the user interface 700 may include one or more object-designation controls such as a stimulation-designation control 710 and an avoid-designation control 712 that, when operated, may cause the user interface 700 to specify a selected selectable object as designated for stimulation (for example, the user-selected selectable object 718) or designated to avoid stimulation (for example, the user-selected selectable object 716), respectively. These two different types of designations, when applied to a selectable object, can be distinguished graphically or visually using, for example, differences in coloring, shading, patterns, or other graphical indicia or any combination thereof. In addition, selectable objects that have not been designated may also be graphically or visually distinguished. In at least some embodiments, the user may select at least one selectable object at a time (for example, via tapping, dragging a finger or cursor over, or circling at least one selectable object in the interface 700). In at least some embodiments, the user may operate at least one of the object-designation controls prior to or subsequent to user selection of at least one selectable object in the interface 700.

Figure 8:
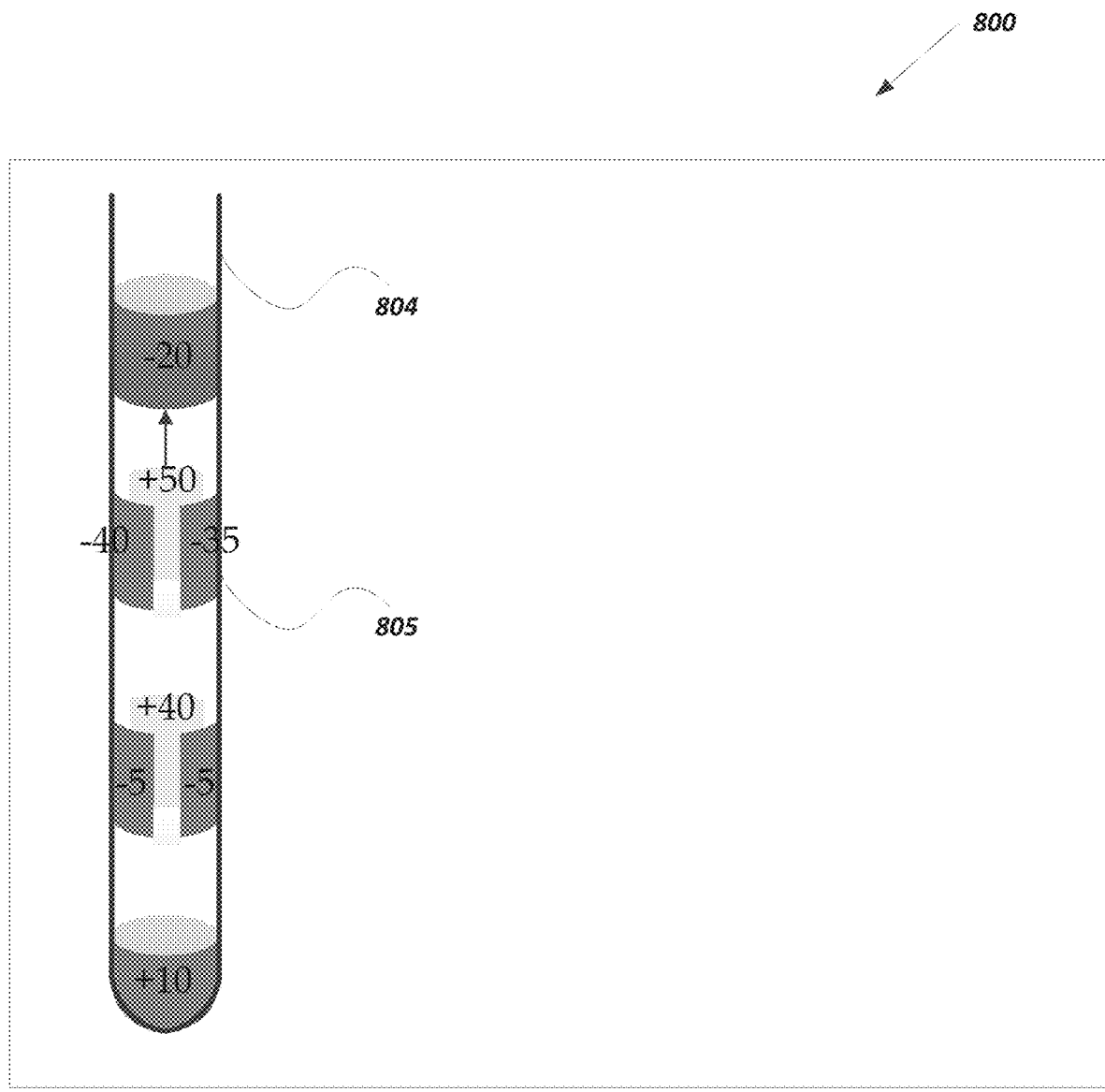
FIG. 8 is a graphical illustration of one embodiment of a user interface for generating at least one fractionalization of at least one stimulation value, according to the invention.

FIG. 8 illustrates an embodiment of a user interface 800 for displaying or modifying a distribution (which can also be referred to as "fractionalization") of current or voltage values between electrodes 805 of a stimulation lead 804. This representation of the lead 804 can be included as an addition to any of the interfaces 400, 500, 600, 700 or may replace the lead representation of those interfaces.

In at least some embodiments, the user interface 800 may include at least one value control for changing the current or voltage values on one or more of the electrodes 805. For example, the user may identify (for example, tap) one of the electrodes 805 of the lead representation 804 and subsequently operate the at least one value control.

Although the user interfaces 400, 500, 600, 700, and 800 of FIGS. 4-8 have been discussed separately, in at least some embodiments, a system may allow a user to select from or shift between two or more of the user interfaces 400, 500, 600, 700, or 800 of FIGS. 4-8.

The user interfaces 400, 500, 600, and 700 of FIGS. 4-7 may include fewer, additional, or alternative user controls. In at least some embodiments, a user interface can have a weight-designation control for use in conjunction with the primitive-designation control, pixel-designation control, or object-designation control to indicate at least one degree of importance or at least one priority to apply to at least one corresponding user-operated designation control. Additionally or alternatively, the weight-designation control may indicate at least one stimulation level (for example, high, medium, or low levels). In at least some embodiments, an interface may include at least one irrelevant-designation control to indicate that it is irrelevant to the objective of the stimulation if the selected pixel, selectable-object, or primitive is stimulated or not.

The user interfaces 400, 500, 600, 700, or 800 of FIGS. 4-8 have been described with respect to two-dimensional planes or grids or other representations, but it will be recognized that the user interfaces may alternatively be related to three-dimensional representations, such as voxels or three-dimensional selectable objects or primitives. The user interface may still display these three-dimensional objects as two-dimensional representations or may provide a three-dimensional or pseudo-three-dimensional representation.

In at least some embodiments, at least one of the user interfaces 400, 500, 600, 700, or 800 of at least one of FIGS. 4-8 may include additional or alternative visual guides. In at least some embodiments, the visual guides may include at least one of SFMs, lines that denote angular planes, lines that denote Z-planes, centroids, or the like. In at least some embodiments, the visual guides may include numerical readouts of, for example, coordinates, dimensions, critical points, or the like.

In at least some embodiments, at least one of the user interfaces 400, 500, 600, 700, or 800 of at least one of FIGS. 4-8 may include additional or alternative user controls. For example, the user controls may include at least one of zoom controls or resolution controls or more generally controls of the virtual camera which render the control scene to the display. In at least some embodiments, user operation of the zoom controls, may cause a user interface to zoom in to or out from at least one portion of the user interface. In at least some embodiments, user operation of the zoom controls or the resolution controls may increase or decrease a resolution of at least one portion of a user interface such as, for example, increasing or decreasing a size of pixels in a pixel grid.

Figure 9:
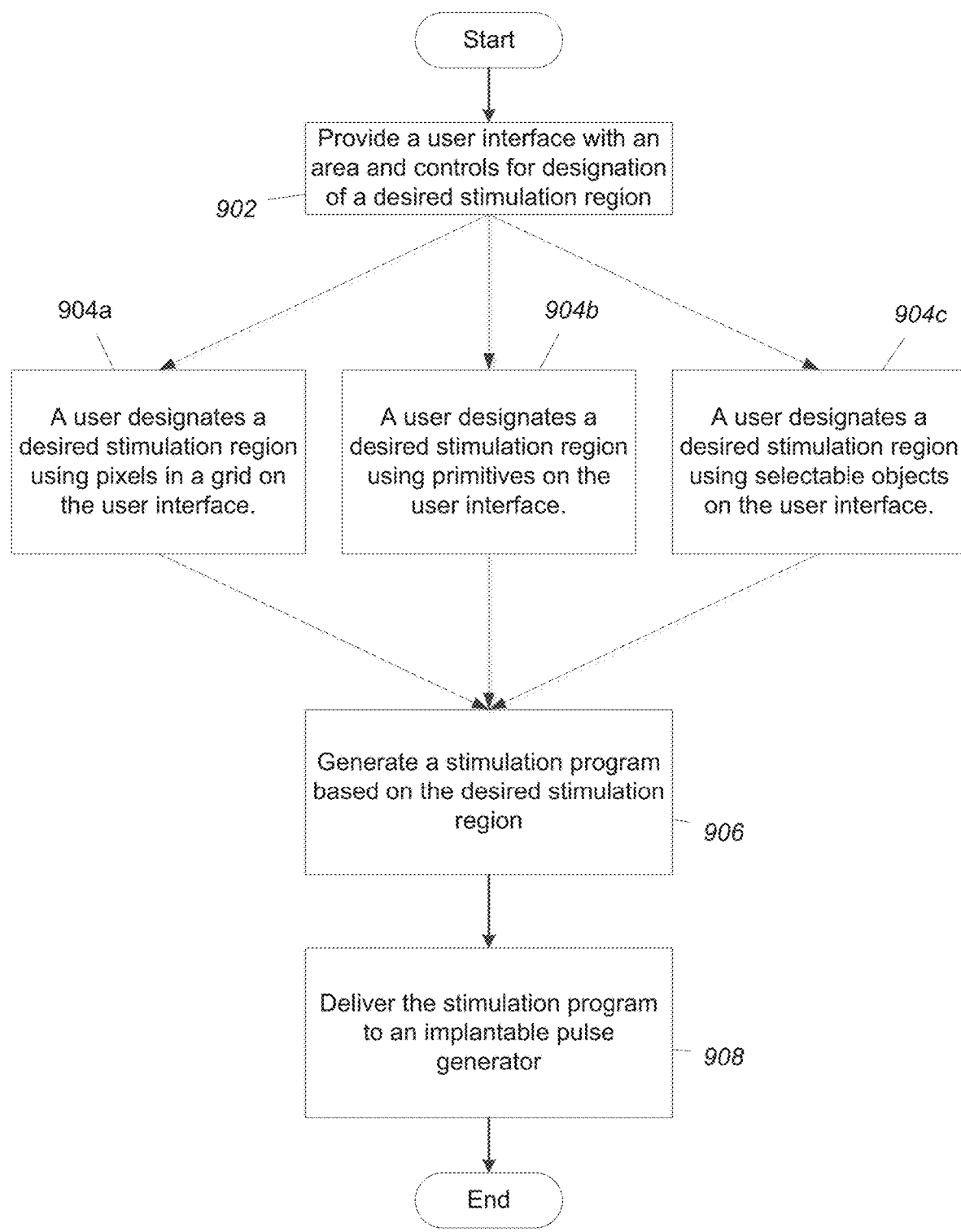
FIG. 9 is a flowchart of one embodiment of a method of generating a stimulation program, according to the invention.

FIG. 9 is a flowchart of one method of generating a stimulation program. In step 902, the processor provides a user interface, such as user interface 400, 500, 600, or 700, that, preferably, has a representation of a portion of a lead (optionally with electrodes represented on the lead), as well as an area around the lead and controls for designating a desired stimulation region.

In steps 904a, 904b, or 904c, the user designates a desired stimulation region within the user interface. In some embodiments, only one of steps 904a, 904b, or 904c is performed. Steps 904a, 904b, and 904c can be considered alternatives to each other. In other embodiments, these steps 904a, 904b, 904c may be used in any combination. For example, the user interface may permit a user to specify a region using a combination of primitives (step 904b) and pixels in a grid (step 904a). As another example, the user interface may permit a user to specify an initial region using primitives (step 904b) and then translate that region into pixels on a grid and allow the user to modify the initial region to the desired region by selecting or deselecting pixels on the grid (step 904a). Any other combination of steps 904a, 904b, and 904c can be used. It will be recognized that the desired stimulation region may be a single, unified region or volume or may be divided in multiple, separate regions or volumes.

It will also be recognized that in any of these steps 904a, 904b, 904c, the designation may be repeated for multiple planes relative to the lead. In some embodiments, movement between the planes can be performed similar to that described with respect to user interface 400 of FIG. 4. For example, the user interface may define a desired stimulation region in plane 406 (FIG. 4) and then define another desired stimulation region in plane 410 (FIG. 4) or any of the other planes. This process can be used to identify a volume for stimulation. In at least some embodiments, the user may specify desired stimulation regions in multiple planes and then the system can interpolate or otherwise determine or estimate the desired stimulation region in other planes (for example, in planes between those planes with regions specified by the user or planes adjacent to those planes with regions specified by the user). In other embodiments, the user may specify at least one desired stimulation region in a single plane and then the system can interpolate or otherwise determine or estimate the desired stimulation region in other planes.

In step 904a, the user designates a desired stimulation region by selecting pixels in one or more grids using, for example, the user interface 600 of FIG. 6. The user may also designate one or more regions for not stimulating.

In step 904b, the user designates a desired stimulation region by placing one or more primitives using, for example, the user interface 500 of FIG. 5. The user may also designate one or more primitives for not stimulating. The user interface may also permit the user to modify the primitives (for example, stretch, compress, move, or the like) as described above with respect to user interface 500 of FIG. 5.

In step 904c, the user designates a desired stimulation region by selecting one or more selectable regions using, for example, the user interface 700 of FIG. 7. The user may also designate one or more selectable regions for not stimulating.

It will be recognized that the user interface may also be used to specify a region to avoid stimulating, as described above with respect to user interfaces 500, 600, 700. One or more steps analogous to steps 904a, 904b, 904c (or any combination thereof) can be used to determine the region to avoid stimulating.

In some embodiments, one or more of the steps 904a, 904b, 904c may be repeated multiple times in an iterative manner to refine a stimulation region or to try different stimulation regions.

In step 906, the at least one computer processor generates at least one stimulation program based, at least in part, on desired stimulation region (and optionally a region to avoid stimulating) obtained using steps 904a, 904b, or 904c (or any combination thereof).

A stimulation program can be described by a set of stimulation parameters that produce the stimulation of the stimulation program. Stimulation parameters can include, but are not limited to, selection of electrode or electrodes to produce the stimulation, stimulation amplitude (total amplitude or individual amplitude for each electrode when multiple electrode are used to produce the stimulation), pulse width, pulse frequency, and the like. Some stimulation programs may also be more complex where the selection of electrodes may change during the program (for example, alternating between a first selection of electrodes and second selection of electrodes) or changes in amplitude, pulse width, pulse frequency, or the like. Also, some stimulation programs may include bursts of stimulation pulses with burst frequency and a pulse frequency.

The stimulation parameters can be used to calculate an estimated region of stimulation. The terms "stimulation field map" (SFM) and "volume of activation" (VOA) are often used to designate an estimated region of tissue that will be stimulated for a particular set of stimulation parameters. Any suitable method for determining the SFM/VOA can be used including those described in, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; and 2015/0066111; and U.S. Provisional Patent Application Ser. No. 62/030,655, all of which are incorporated herein by reference. In some embodiments, a SFM/VOA may also be determined by methods other than calculation such as, for example, observations of stimulation effects, observations from internal or external sensors, imaging (e.g., MRI), or the like.

In at least some embodiments, the stimulation program is determined by selecting stimulation parameters that produce a SFM/VOA that matches the desired stimulation region within a predetermined degree or tolerance or that best matches the desired stimulation region. This may include, for example, selecting an initial set of stimulation parameters, calculating a SFM/VOA using those stimulation parameters, comparing that SFM/VOA to the desired stimulation region, and then refining the set of stimulation parameters in view of the comparison. This procedure can be iterated until a suitable set of stimulation parameters for a stimulation program are determined.

In addition, when a region to be avoided is also determined, the overlap between the region to be avoided and the calculated SFM/VOA may also be taken into account in refining the stimulation parameters. Moreover, in at least some embodiments, a suitable set of stimulation parameters will not overlap with the region to be avoided by at least some threshold amount, percentage, or other suitable measure of overlap.

In at least some embodiments, instead of calculating a SFM/VOA, stimulation parameters with an associated stimulation region (such as a SFM/VOA that has been previously calculated or otherwise determined) may be retrieved from an internal or external memory and compared to the desired stimulation region. For example, the system may use a database of stimulation parameters and associated stimulation regions to select the stimulation program (with its stimulation parameters) based on matching the database information with the desired stimulation region. Again, a determined region to be avoided may also be incorporated in this procedure for determination of the stimulation program.

In addition, in at least some embodiments, the user interface may provide controls by which the user may also manually alter one or more of the stimulation parameters for the stimulation program.

In at least some embodiments, the user interface may display the stimulation region for the stimulation program in relation to the desired stimulation region (and, optionally, the identified region to be avoided) to allow the user to visually observe the match between the regions.

In step 908, the at least one computer processor may deliver the stimulation program to an implantable pulse generator, ETS, or other device of an implantable electrical stimulation system. In at least some embodiments, the computer processor may initiate a signal that provides the implantable pulse generator, or other device, with the stimulation program for producing electrical stimulation to the patient in accordance with the stimulation program when selected.

In at least some embodiments, at least one of steps 902, 904*a*, 904*b*, 904*c*, 906, and 908 is skipped.

Figure 10:
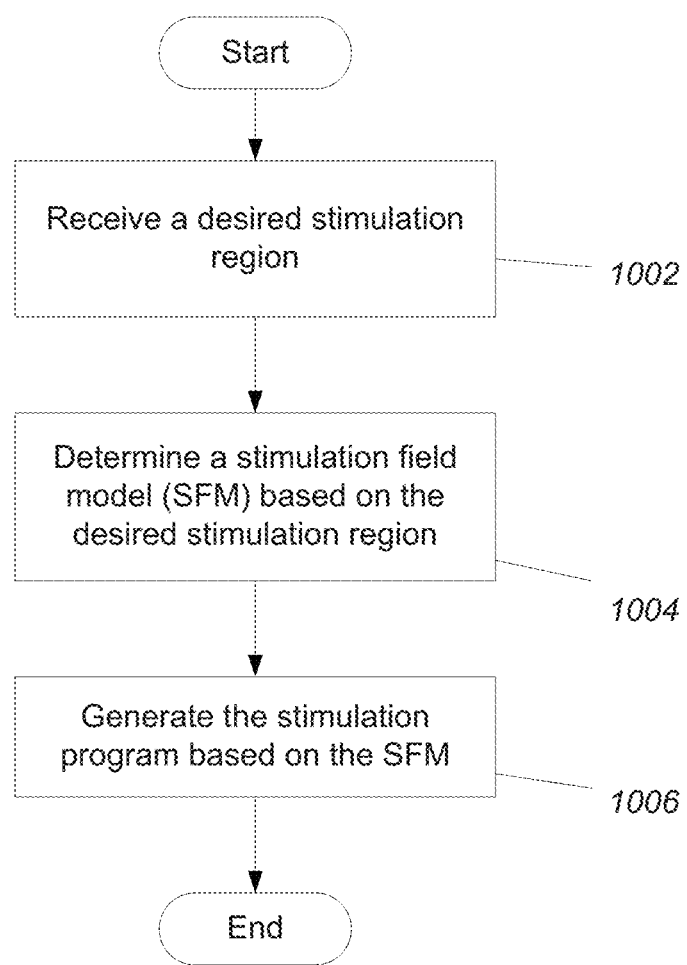
FIG. 10 is a diagrammatic illustration of another embodiment of a method of generating a stimulation program, according to the invention.

FIG. 10 illustrates a flowchart of one embodiment of a method of generating a stimulation program according to step 906 of FIG. 9. In at least some embodiments, the at least one computer processor may execute the method instead of or in addition to at least one portion of step 906 of FIG. 9.

In step 1002, a desired stimulation region is received. The desired stimulation region may be based, at least in part, on at least one of user-selected pixels, a user-placed primitive, or a user-selected selectable object or any combination thereof as described above with respect to steps 904*a*, 904*b*, 904*c*. In some embodiments, a region to be avoided can also be designated. In some embodiments, multiple regions may be designated.

In some embodiments, the stimulation region (or region to be avoided) can be a volume defined by the user in using one plane or multiple planes. For example, the system may determine that the desired stimulation region extends from a designated region on a first plane to one or more other planes. In some embodiments, the system (automatically or under user direction) may uniformly extend the desired stimulation region around (partially or entirely) the lead to form a volume. For example, based on a ring electrode or a circumferentially elongated segmented electrode, the system may uniformly extend the desired stimulation region around the portion of the lead that the electrode covers. As another example, this same process may also be used based on a user-input command to uniformly employ segmented electrodes that are aligned with each other along the circumference of the lead. In at least some embodiments, this same processes may also be used (automatically or based on a user-input command) for longitudinally elongated electrodes or electrodes that are aligned with each other along the longitudinal length of the lead. In other embodiments, the system (automatically or under user direction) may decrease at least one dimension of the shape around the lead. In yet other embodiments, where a desired stimulation region is determined in more than one plane, the system may interpolate or estimate the stimulation volume between those planes. It will be understood that these same processes may also be used for a region to be avoided.

In at least some embodiments, the system may model the desired region or volume derived from the desired region using a predefined or stereotypical volume. For example, the stereotypical volume may include at least one three-dimensional shape such as, for example ovoid, ellipsoid, tube, Gaussian distributions, or Poisson distributions. The at least one three-dimensional shape may include a set or series of two-dimensional shapes such as, for example, Gaussian distributions, Poisson distributions, planar shapes, or cross-sections. For example, the two-dimensional shapes may be slices of the three-dimensional shapes. As another example, the two-dimensional shapes may include three or more shapes or planar faces that define outer boundaries of at least one closed volume. In at least some embodiments, the stereotypical volume may be defined by at least one of a center of mass, a major axis, a minor axis, a vertex, a mean in principal axes, a variance in principal axes, or spatial relationship to the lead representation.

In step 1004, a stimulation field model (SFM) or Volume of Activation (VOA) is determined based on the desired stimulation region. Any suitable method for determining the SFM/VOA can be used including those described in, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; and 2015/0066111; and U.S. Provisional Patent Application Ser. No. 62/030,655, all of which are incorporated herein by reference. In particular, the system can calculate one or more SFMs/VOAs that approximate the desired stimulation region. Alternatively, the system may access a SFM library or database stored in memory internal or external to the system. In at least some embodiments, the library may, additionally or alternatively to SFMs, contain at least one other stimulation configuration such as, for example, stimulation parameters, electrode patterns, or the like.

In at least some embodiments, the system may select from one or more SFMs/VOAs that are calculated or retrieved based on how closely the SFM/VOA matches to the desired stimulation region. For example, searching for the closest match may include volume matching. It will also be understood, that for embodiments where a region to avoid stimulation is determined, the matching may also take a degree of overlap of each candidate SFM/VOA with the region to avoid into account (e.g., the system may require no overlap or no more than a particular degree or percentage overlap). In at least some embodiments, at least one of the desired region or the candidate SFM/VOA may be rotated for comparison to each other.

Any suitable metric may be used for determining the degree of matching between the desired stimulation region and an SFM/VOA. For example, a degree of matching may be determined using a distance metric. One example of a suitable distance metric is a sum of total differences between selected points on a surface or boundary of the desired stimulation region and analogous points on the SFM/VOA. The points may be uniformly or nonuniformly distributed or may be (or at least include) one or more critical points such as inflection/local maximum/local minimum points on the surface or boundary, surface or boundary points associated with lines radiating from a center or center of mass of the region or volume, or special points associated with particular shapes (for example, elliptical foci).

Another example of suitable distance metric represents the region or volume, as well as the SFM/VOA, by one or more m×n matrices of values where each matrix corresponds to a two-dimensional region of space (similar to the grid 608 in FIG. 6). These values can be 1 or 0 in some embodiments to indicate within the region or volume or outside the region or volume, respectively. In other embodiments, a wider range of values can be used including positive numbers to indicate where stimulation is desirable and, possibly a degree of desirability (e.g., a "2" is more desirable than a "1"), and negative numbers indicate where stimulation is to be voided, possibly with a degree of avoidance. The distance metric is then a sum over the entries of the matrix of the difference between the entry for the desired stimulation region and the entry for the SFM/VOA. For example, an equation for distance, D, with entries, x, can be $D=\Sigma_{j=1}^{n}\Sigma_{i=1}^{m}|x_{i,j,desired}-x_{i,j,SFM/VOA}|$. This equation may also be summed over multiple matrices representing multiple two-dimensional regions of space (such as planes 406, 410 of FIG. 4).

As another distance metric, the region or volumes, as well as the SFM/VOA, are represented by one or more m×n matrices of values where each matrix corresponds to a two-dimensional region of space (similar to the grid 608 in FIG. 6). The value of 1 in the matrix corresponds to an edge of the region/volume/SFM/VOA and the value of 0 are non-edge spatial areas. The distance metric is then a sum over the entries of the matrix of the difference between the entry for the desired stimulation region and the entry for the SFM/VOA. For example, an equation for distance, D, with entries, x, can be $D=\Sigma_{j=1}^{n}\Sigma_{i=1}^{m}|x_{i,j,desired}-x_{i,j,SFM/VOA}|$. This equation may also be summed over multiple matrices representing multiple two-dimensional regions of space (such as planes 406, 410 of FIG. 4). This particular distance metric is related to how well the edges of the SFM/VOA match those of the desired stimulation region.

When the desired region of stimulation and SFM/VOA have similar shapes, other metrics can be used based on those shapes. For example, a distance metric may be a spatial distance between center of mass coordinates of the desired stimulation region and the SFM/VOA, a difference in volumes or a weighted difference in axes (e.g., length cubed to represent contributions of axes to volume, or length squared to target area), differences in cross-sectional area contours, or the like.

In some embodiments, an SFM/VOA may be selected from a number of different SFMs/VOAs based on having a most favorable distance metric. In some embodiments, a SFM/VOA may be selected because it has a distance metric that is below a threshold value. Other methods of selection may also be used. In addition, where a region to avoid stimulation is also determined, the selection may also take into account the degree of overlap with the region to avoid (e.g., the system may require no overlap or no more than a particular degree or percentage overlap) and may reject an otherwise acceptable SFM/VOA based on the unacceptable overlap with the region to avoid.

In step 1006, the system generates stimulation program based on the determined SFM/VOA. Generally, the SFM/VOA is calculated or associated with a particular set of stimulation parameters.

In any of the systems and methods described above, when the computing device 300 generates the stimulation program, the computing device 300 may communicate at least one of the set of stimulation parameters or the stimulation program to the IPG 14, the ETS 20, or another device.

It will be understood that the system can include at least one of the methods described hereinabove with respect to FIGS. 9 and 10 in any combination. In at least some embodiments, the at least one computer processor may iteratively execute at least one portion of at least one of the methods of FIGS. 9 and 10 in parallel to or during execution of at least one other portion of at least one of the methods of FIGS. 9 and 10. In at least some embodiments, the at least one computer processor may execute at least one portion of at least one of the methods of FIGS. 9 and 10 in real-time (for example, responsive to each of user selection, placement, modification, or other input command). In at least some embodiments, the at least one computer processor may execute at least one portion of at least one of the methods of FIGS. 9 and 10 responsive to confirmation that the user has completed making inputs for generating a stimulation program.

The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, at least one process may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the structure, manufacture, and use of the invention. Since many embodiments of the invention can be made without depart-

What is claimed as new and desired to be protected by Letters Patent of the United States is:

1. A method for generating a stimulation program for electrical stimulation of a patient, the method comprising:
   providing, by a processor on a display communicatively coupled to the processor, a first grid with gridlines demarcating a plurality of selectable first pixels and a representation of a portion of an electrical stimulation lead with a plurality of electrodes;
   obtaining, by the processor, a user selection of a first plurality of the first pixels in the first grid of first pixels for stimulation;
   generating, by the processor, a stimulation program based, at least in part, on the user-selected first plurality of the first pixels for stimulation using at least one of the electrodes of the electrical stimulation lead; and
   initiating, by the processor, a signal that provides an implantable pulse generator with the stimulation program for producing electrical stimulation using an electrical stimulation lead coupled to the implantable pulse generator in accordance with the stimulation program.

2. The method of claim 1, wherein generating the stimulation program comprises:
   determining, by the processor, a target volume based, at least in part, on the user-selected first plurality of the first pixels for stimulation;
   determining, by the processor, a stimulation field model (SFM) based, at least in part, on the determined target volume; and
   generating, by the processor, the stimulation program based, at least in part, on the SFM.

3. The method of claim 2, further comprising:
   providing, by the processor on the display, a second grid demarcating a plurality of selectable second pixels, the second grid of second pixels residing on a different plane than a plane on which the first grid of first pixels resides; and
   obtaining, by the processor, a user selection of a plurality of the second pixels in the second grid of second pixels for stimulation,
   wherein determining the target volume comprises determining, by the processor, the target volume based, at least in part, on both the user-selected first plurality of the first pixels for stimulation and the user-selected plurality of the second pixels for stimulation.

4. The method of claim 1, wherein providing the first grid of first pixels comprises providing, by the processor on the display, a view of the first grid of first pixels, wherein the view shows the first grid of first pixels in relation to a representation of at least one anatomical or physiological feature.

5. The method of claim 1, further comprising obtaining, by the processor, a user selection of a second plurality of the first pixels in the first grid of first pixels to avoid stimulation, wherein generating the stimulation program comprises:
   determining, by the processor, a first volume based, at least in part, on the user-selected first plurality of the first pixels for stimulation;
   determining, by the processor, a second volume based, at least in part, on the user-selected second plurality of the first pixels to avoid stimulation;
   determining, by the processor, a stimulation field model (SFM) based, at least in part, on the first and second determined volumes; and
   generating, by the processor, the stimulation program based, at least in part, on the SFM.

6. The method of claim 1, wherein generating the stimulation program comprises:
   matching, by the processor, the user-selected first plurality of the first pixels for stimulation to a stimulation field model (SFM) stored in a memory communicatively coupled to the processor;
   selecting, by the processor, at least one of the electrodes of the electrical stimulation lead based, at least in part, on the SFM;
   selecting, by the processor, a set of stimulation parameters based, at least in part, on the SFM; and
   generating, by the processor, the stimulation program.

7. The method of claim 1, further comprising obtaining, by the processor, a user input representing a stimulation level for each one of the user-selected first plurality of the first pixels for stimulation,
   wherein generating the stimulation program comprises generating, by the processor, the stimulation program based, at least in part, on the user-selected first plurality of the first pixels for stimulation and on the user-input stimulation level for each one of the user-selected first plurality of the first pixels for stimulation.

8. The method of claim 1, further comprising superimposing the first grid of first pixels on a representation of at least one anatomical or physiological feature.

9. A non-transitory computer-readable medium having computer executable instructions stored thereon that, when executed by at least one processor, cause the at least one processor to perform the method of claim 1.

10. A system for a stimulation program for electrical stimulation of a patient, the system comprising a processor configured and arranged to perform the method of claim 1.

11. A method for generating a stimulation program for electrical stimulation of a patient using an electrical stimulation lead, the method comprising:
   providing, by processor on a display communicatively coupled to the processor, a portion of a first plane defined along one side by a longitudinal axis of the electrical stimulation lead;
   obtaining, by the processor, a user selection of a first primitive from a plurality of potential-primitive controls and placement of the first primitive onto the first plane for stimulation, wherein each of the potential-primitive controls corresponds to a predetermined regular or irregular shape;
   obtaining, by the processor, a user input of a command to modify at least one feature of the user-placed first primitive for stimulation;
   providing, by the processor on the display, a portion of a second plane, wherein the second plane is different from the first plane and is rotated, with respect to the longitudinal axis of the electrical stimulation lead, by an angle of less than 90 degrees from the first plane;
   obtaining, by the processor, a user selection of a second primitive from the plurality of potential-primitive controls and placement of the second primitive onto the second plane;
   generating, by the processor, a stimulation program based, at least in part, on the modified user-placed first primitive and the user-placed second primitive for stimulation; and
   initiating, by the processor, a signal that provides an implantable pulse generator with the stimulation program for producing electrical stimulation using an electrical stimulation lead coupled to the implantable pulse generator in accordance with the stimulation program.

12. The method of claim 11, wherein generating the stimulation program comprises:
    determining, by the processor, a target volume based, at least in part, on the modified user-placed first primitive and the user-placed second primitive for stimulation;
    determining, by the processor, a stimulation field model (SFM) based, at least in part, on the determined target volume; and
    generating, by the processor, the stimulation program based, at least in part, on the SFM.

13. The method of claim 12, further comprising:
    obtaining, by the processor, a user input of a command to modify at least one feature of the user-placed second primitive for stimulation,
    wherein determining the target volume comprises determining, by the processor, the target volume based, at least in part, on both the modified user-placed first primitive for stimulation and the modified user-placed second primitive for stimulation.

14. The method of claim 11, wherein obtaining the user input of the command to modify the at least one feature of the user-placed first primitive for stimulation comprises obtaining, by the processor, a user input of a command to alter a shape of the user-placed first primitive for stimulation along at least one dimension of the user-placed first primitive for stimulation.

15. The method of claim 11,
    wherein generating the stimulation program comprises:
        determining, by the processor, a first volume based, at least in part, on the modified user-placed first primitive for stimulation;
        determining, by the processor, a second volume based, at least in part, on the user-placed second primitive to avoid stimulation;
        determining, by the processor, a stimulation field model (SFM) based, at least in part, on the first and second determined volumes; and
        generating, by the processor, the stimulation program based, at least in part, on the SFM, wherein the stimulation program, when implemented by the implantable pulse generator, causes the implantable pulse generator to stimulate the first determined volume and to avoid stimulation of the second determined volume.

16. The method of claim 15, wherein:
    determining the SFM comprises determining when the second determined volume overlaps at least one portion of first determined volume; and
    generating the stimulation program based, at least in part, on the SFM comprises, responsive to the second determined volume overlapping the at least one portion of the first determined volume, generating, by the processor, the stimulation program based, at least in part, on the SFM, wherein the stimulation program, when implemented by the implantable pulse generator, causes the implantable pulse generator to stimulate at least one portion of the first determined volume that the second determined volume fails to overlap and to avoid stimulation of at least one portion of the second determined volume.

17. The method of claim 15, further comprising obtaining, by the processor, a user input of a command to modify at least one feature of the user-placed second primitive to avoid stimulation,
    wherein determining the second volume comprises determining, by the processor, the second volume based, at least in part, on the modified user-placed second primitive to avoid stimulation.

18. The method of claim 11, wherein generating the stimulation program comprises:
    matching, by the processor, the modified user-placed first primitive to a stimulation field model (SFM) stored in a memory communicatively coupled to the processor;
    selecting, by the processor, a set of stimulation electrodes from the electrodes of the electrical stimulation lead based, at least in part, on the SFM;
    selecting, by the processor, a set of stimulation parameters based, at least in part, on the SFM; and
    generating, by the processor, the stimulation program, wherein the stimulation program, when implemented by the implantable pulse generator, causes the implantable pulse generator to stimulate the patient via the set of stimulation electrodes according to the set of stimulation parameters.

19. A non-transitory computer-readable medium having computer executable instructions stored thereon that, when executed by at least one processor, cause the at least one processor to perform the method of claim 11.

20. A system for generating a stimulation program for electrical stimulation of a patient, the system comprising processor configured and arranged to perform the method of claim 11.

* * * * *